US009713524B2

(12) United States Patent
Glicksman

(10) Patent No.: US 9,713,524 B2
(45) Date of Patent: Jul. 25, 2017

(54) HUMAN IMPLANTABLE TISSUE EXPANDERS

(71) Applicant: IMPLITE LTD., Petah Tikva (IL)

(72) Inventor: Ami Glicksman, Petah Tikva (IL)

(73) Assignee: IMPLITE LTD., Petah Tikva (IL)

( * ) Notice: Subject to any disclaimer, the term of this patent is extended or adjusted under 35 U.S.C. 154(b) by 0 days.

(21) Appl. No.: 14/762,469

(22) PCT Filed: Jan. 29, 2014

(86) PCT No.: PCT/IL2014/050097

§ 371 (c)(1), (2) Date: Jul. 22, 2015

(87) PCT Pub. No.: WO2014/118773

PCT Pub. Date: Aug. 7, 2014

(65) Prior Publication Data

US 2015/0351900 A1 Dec. 10, 2015

Related U.S. Application Data

(60) Provisional application No. 61/758,286, filed on Jan. 30, 2013, provisional application No. 61/781,158, filed on Mar. 14, 2013.

(51) Int. Cl.
*A61F 2/12* (2006.01)
*A61B 90/90* (2016.01)

(52) U.S. Cl.
CPC ................ *A61F 2/12* (2013.01); *A61B 90/90* (2016.02); *A61F 2210/0061* (2013.01); *A61F 2210/0076* (2013.01); *A61F 2230/0063* (2013.01); *A61F 2230/0076* (2013.01); *A61F 2230/0091* (2013.01)

(58) Field of Classification Search
CPC ........................................................ A61F 2/12
USPC ........................................................ 623/7–8
See application file for complete search history.

(56) References Cited

U.S. PATENT DOCUMENTS

| | | | |
|---|---|---|---|
| 3,366,975 | A | 2/1968 | Pangman |
| 3,683,424 | A | 8/1972 | Pangman |
| 3,934,274 | A | 1/1976 | Hartley, Jr. |
| 3,986,213 | A | 10/1976 | Lynch |
| 4,178,643 | A | 12/1979 | Cox, Jr. |
| 4,298,998 | A | 11/1981 | Naficy |
| 4,430,764 | A | 2/1984 | Finkelstein |
| 4,507,810 | A | 4/1985 | Bartholdson |
| 4,624,671 | A | 11/1986 | Kress |
| 4,650,487 | A | 3/1987 | Chaglassian |

(Continued)

FOREIGN PATENT DOCUMENTS

| | | |
|---|---|---|
| CN | 2274042 | 2/1998 |
| CN | 1403065 | 3/2003 |

(Continued)

*Primary Examiner* — Suzette J Gherbi
(74) *Attorney, Agent, or Firm* — The Roy Gross Law Firm, LLC; Roy Gross

(57) ABSTRACT

Human implantable tissue expanders are provided, that comprise an inner foam filling enclosed within a substantially non-stretchable resilient expansion restricting layer configured to retain a shape and/or volume of said foam filling upon changes of ambient pressure and/or temperature, and an outer shell comprising one or more layers formed of a resilient material.

16 Claims, 11 Drawing Sheets

204
200
206
208
216
210
212
214
202

(56) References Cited

U.S. PATENT DOCUMENTS 4,651,717 A 3/1987 Jakubczak
4,685,447 A 8/1987 Iversen
4,773,908 A 9/1988 Becker
4,773,909 A 9/1988 Chaglassian
4,790,848 A 12/1988 Cronin
4,944,749 A 7/1990 Becker
5,060,328 A 10/1991 Larson
5,074,878 A 12/1991 Bark
5,092,882 A 3/1992 Lynn
5,104,409 A 4/1992 Baker
5,110,653 A 5/1992 Landi
5,122,405 A 6/1992 Landi
5,137,769 A 8/1992 Landi
5,159,725 A 11/1992 Larson
5,180,619 A 1/1993 Landi
5,203,607 A 4/1993 Landi
5,236,454 A 8/1993 Miller
5,246,454 A 9/1993 Peterson
5,282,856 A 2/1994 Ledergerber
5,340,352 A 8/1994 Nakanishi
5,358,521 A 10/1994 Shane
5,376,117 A 12/1994 Pinchuk
5,437,824 A 8/1995 Carlisle
5,496,367 A 3/1996 Fisher
5,496,610 A 3/1996 Landi
5,500,019 A 3/1996 Johnson
5,509,484 A 4/1996 Landi
5,534,343 A 7/1996 Landi
5,545,217 A 8/1996 Offray
5,617,595 A 4/1997 Landi
5,658,330 A 8/1997 Carlisle
5,701,621 A 12/1997 Landi
5,824,081 A 10/1998 Knapp
5,836,871 A 11/1998 Wallace
5,840,397 A 11/1998 Landi
5,840,400 A 11/1998 Landi
5,882,353 A 3/1999 VanBeek
5,902,335 A 5/1999 Snyder, Jr.
5,961,552 A 10/1999 Iversen
6,066,220 A 5/2000 Schneider-Nieskens
6,183,514 B1 2/2001 Becker
6,187,043 B1 * 2/2001 Ledergerber .......... A61F 2/0077 623/11.11
6,206,930 B1 3/2001 Burg
6,214,045 B1 4/2001 Corbitt, Jr.
6,228,116 B1 5/2001 Ledergerber
6,315,796 B1 11/2001 Eaton
6,415,583 B1 7/2002 Landi
6,432,138 B1 8/2002 Offray
6,544,287 B1 4/2003 Johnson
6,605,116 B2 8/2003 Falcon
6,802,861 B1 10/2004 Hamas
6,811,570 B1 11/2004 Gehl
6,875,233 B1 4/2005 Turner
6,932,840 B1 8/2005 Bretz
8,070,768 B2 * 12/2011 Kim ........................ A61F 5/003 600/37
8,236,054 B2 8/2012 Purkait
8,394,118 B2 * 3/2013 Jones ..................... A61B 90/02 606/192
8,545,557 B2 10/2013 Glicksman
2001/0010024 A1 7/2001 Ledergerber
2002/0038147 A1 3/2002 Miller
2002/0143396 A1 10/2002 Falcon
2003/0040806 A1 2/2003 MacDonald
2003/0074084 A1 4/2003 Nakao
2003/0149481 A1 8/2003 Guest
2004/0148024 A1 7/2004 Williams
2004/0153151 A1 8/2004 Gonzales De Vicente
2004/0162613 A1 8/2004 Roballey
2004/0176841 A1 9/2004 Ferguson
2006/0264399 A1 11/2006 Lim
2006/0282164 A1 12/2006 Seastrom
2007/0299541 A1 12/2007 Chernomorsky
2008/0221679 A1 9/2008 Hamas
2009/0048684 A1 2/2009 Lesh
2009/0093878 A1 4/2009 Glicksman
2009/0299473 A1 12/2009 Govrin-Yehudian
2010/0114311 A1 5/2010 Becker
2010/0114312 A1 5/2010 Glicksman
2011/0054606 A1 * 3/2011 Forsell ...................... A61F 2/12 623/8
2011/0196195 A1 * 8/2011 Raven ................... A61F 5/0056 600/37
2011/0208302 A1 8/2011 Glicksman
2011/0264213 A1 * 10/2011 DeMiranda ............... A61F 2/12 623/8
2011/0288639 A1 11/2011 Trilokekar
2011/0306827 A1 * 12/2011 Chitre ....................... A61F 2/12 600/37
2011/0309541 A1 * 12/2011 Thompson .............. A61L 27/18 264/46.6
2012/0078366 A1 3/2012 Jones
2012/0116509 A1 5/2012 Forsell
2012/0165934 A1 6/2012 Schuessler
2012/0226352 A1 9/2012 Becker
2013/0325119 A1 * 12/2013 Mojaradi .................. A61F 2/12 623/8
2014/0156001 A1 * 6/2014 Davodian ................. A61F 2/12 623/8
2014/0277440 A1 * 9/2014 Martin ...................... A61F 2/12 623/8
2016/0000551 A1 * 1/2016 Khouri .................. A61F 13/145 623/23.7
2016/0074152 A1 * 3/2016 Chitre ....................... A61F 2/12 623/8

FOREIGN PATENT DOCUMENTS

CN 101199867 6/2008
CN 101919749 12/2010
EP 0054359 6/1982
EP 1510189 3/2005
EP 1820473 8/2007
EP 2387971 11/2011
FR 2859098 3/2005
FR 2862523 5/2005
JP S5815612 1/1983
JP 11-503652 3/1999
JP 2001-519203 10/2001
JP 20041130118 4/2004
JP 2005-137398 6/2005
RU 02332188 8/2008
WO 98/10803 3/1998
WO 99/20319 4/1999
WO 01/66039 9/2001
WO 2006/114786 11/2006
WO 2007/000756 1/2007
WO 2007/004213 1/2007
WO 2008/038851 4/2008
WO 2008/081439 7/2008
WO 2010/049926 5/2010
WO 2011/081826 7/2011
WO 2011/086537 7/2011
WO 2016/092538 6/2016
WO 2016/108228 7/2016

* cited by examiner 200
212
214
210
216
208
206

200

IIH
IIH
220
230

204

200
206
216
208
210
212
214
202

HUMAN IMPLANTABLE TISSUE EXPANDERS

RELATED APPLICATION DATA

This application is the U.S. National Stage of International Application No. PCT/IL2014/050097 filed Jan. 29, 2014, which claims the benefit of U.S. Provisional Patent Application No. 61/758,286 filed Jan. 30, 2013, and U.S. Provisional Patent Application No. 61/781,158 filed Mar. 14, 2013. Each of the foregoing applications is hereby incorporated by reference in its entirety for all purposes.

FIELD OF THE INVENTION

The present invention relates to human implantable tissue expanders, suitable, inter alia, for augmentation or reconstruction of breast, pectorals, calf muscles and other soft tissue defects.

BACKGROUND OF THE INVENTION

Soft-tissue implants are used in various locations in the human body. The most common use is for reconstructing or improving the normal body contour or augmenting the female breast. The most common breast prostheses generally include a flexible elastomeric shell or envelope, typically made of silicone, which is filled with a soft gel, mainly silicone gel, a saline solution or a combination of both.

U.S. Pat. No. 3,683,424 discloses a compound prosthesis that has an elastic sack or envelope which contains an open-cells foam core and a quantity of a liquid in the cells of the core. The envelope has a flexible tube for adding the liquid at time of implantation so the size of the implant can be adjusted as desired.

U.S. Pat. No. 4,298,998 discloses a breast prosthesis claiming to overcome the tightness and contracture of the fibrous capsule which forms around an existing prosthesis. The construction of the prosthesis causes the capsule to form at a predetermined, controlled distance from the surface thereof. This prosthesis is constructed with a first phase or outer temporary component and a second phase or inner permanent component. The inner component is a container or sac of a flexible, non-absorbable material filled with a fluid or gel filler material. The temporary outer component is an outer container or cover of a material which is absorbable under the conditions of use, and an inert filler material, preferably an absorbable, biologically acceptable liquid, e.g. saline solution, filling the space between the inner and outer components.

U.S. Pat. No. 4,650,487 discloses a surgically implantable, multi-lumen, high profile mammary implant which includes a first, flexible, elastic lumen at least partly filled with a soft gel material and having a front wall approximating the shape of a human breast and a second, firmer, flexible lumen within the first lumen and connected thereto solely at the rear wall of the first lumen. A third lumen preferably inflatable surrounds the first lumen and is inflated with saline solution.

U.S. Pat. No. 5,236,454 discloses an implantable stacked breast prosthesis comprising two or more separate chambers stacked on each other, and fastened together eccentrically, so as to give a normal contour to the reconstructed or augmented breast and to prevent slippage of the chambers. At least one of the chambers is collapsed and may be variably filled with liquid.

U.S. Pat. No. 5,358,521 discloses a multi-layer prosthesis that simulates tissue tactility by structuring the plurality of layers of material making up the prosthesis to include lubricant coating between the layers. It is the plurality of layers and the lubricity of their movement which contributes greatly to the tactile simulation of human tissue. Present in the prosthesis is a ballast lumen which moves freely and contributes mass and motility to the prosthesis.

U.S. Pat. No. 5,376,117 discloses breast prostheses for subcutaneous implantation for breast augmentation. The prostheses include an outer shell having a smooth non-porous outer envelope and a non-woven porous outer layer affixed to the envelope.

U.S. Pat. No. 5,437,824 discloses a breast prosthesis for implantation beneath the skin. In one preferred embodiment the prosthesis has an outer elastic shell which encloses a biocompatible fluid and a silicone foam insert of unitary construction having the shape and approximate consistency and tactility of breast tissue. The foam insert occupies substantially the entire volume enclosed by the shell of the implantable prosthesis and consists of a foam body that is molded to the shape of the breast. In another preferred embodiment only a portion of the volume enclosed by the cell is occupied by the foam insert. In yet another embodiment a foam insert comprising an open-cell and closed-cell foam body may directly implanted beneath the skin for breast augmentation or reconstruction without a shell.

U.S. Pat. No. 5,824,081 discloses a tissue implant having visco-elastic characteristics which simulate the natural tissue that is intended to be augmented or replaced. The implant is comprised of a shell or envelope enclosing a compound foam body and a fluid filler material.

U.S. Pat. No. 6,187,043 discloses an implant and coverings for an implant for use in the human body. Coverings for implants are constructed to present a biocompatible surface to the body and to provide a textured surface which serves to disorganize scar tissue which forms around the implant.

U.S. Pat. No. 6,875,233 discloses a hinging breast implant capable a being variably sized and that includes an exterior shell and an inner bladder. The exterior shell is typically a bellows having a plurality of pleats so that the outer size of the implant is variable so that different sizes and shapes can be obtained. The inner bladder can be filled with a suitable filling material, liquid, gas or solid. As the bladder is filled, the exterior shell expands in a manner that creates a lifting effect and a ballooning effect.

U.S. Pat. No. 8,236,054 discloses an implantable soft tissue prosthesis comprising a hollow shell formed of a flexible elastomeric envelope, the shell having an inner volume and an exterior surface, when the inner volume is filled with an elastomeric silicone tubing that is preshaped conforming to the inner volume of the shell, the prosthesis being adapted to be surgically implanted in a human breast.

US 2002/0038147 discloses an improved permanently implantable breast tissue prosthesis comprising angularly and immutably attached base and dome envelopes wherein the base envelope is of a substantially triangular shape and the dome envelope is of a substantially discoid shape, each envelope having a shell defining an inner fluid containable chamber and an outer textured surface to be in direct contact with breast tissue and a valve formed as a part of a wall in base and dome envelopes, the valve facilitating the introduction, containment or removal of fluid within the containable chamber of each envelope.

US 2004/0162613 discloses a cosmetic and reconstructive prosthesis containing a rupture indicator, which includes an external envelope of medical grade elastomer containing a fluid material and a biologically compatible chemical indicator for indicating rupture of the prosthesis, and an internal envelope of medical grade elastomer disposed within the external envelope, the internal envelope containing an implant filling material.

WO 2007/000756, to the inventor of the present invention, discloses, inter alia, a human implantable tissue expander comprising a flexible enclosure for at least one material having at least one fluid flow characteristic; and a flexible and resilient skeleton associated with said flexible enclosure and being operative to maintain said flexible enclosure in a predetermined three-dimensional configuration generally independently of its orientation relative to gravitational acceleration.

WO 2008/081439, to the inventor of the present invention and others, discloses, inter alia, an implantable tissue expander including an internal skeletal element extending between a base surface and an outer surface and including at least one plurality of elongate cells extending along mutually generally parallel axes from the base surface to the outer surface and being defined by elongate cell walls formed of a resilient material; and a sealed enclosure, sealing the internal skeletal element and adapted for preventing body fluids from filling the plurality of elongate cells.

WO 2010/049926, to the inventor of the present invention, discloses, inter alia, a reconstructive breast prosthesis suitable for implantation into a void in a breast following a lumpectomy procedure in which a body of tissue is excised from the breast, the reconstructive breast prosthesis including an implant body at least generally configured to assume an implant shape corresponding to the shape of the body of tissue excised from the breast and an implant shape retaining structure adapted to maintain the implant body in the implant shape, the reconstructive breast prosthesis having an overall density which is less than the density of the body of tissue excised from the breast.

There still remains a need for improved implantable tissue expanders.

SUMMARY OF THE INVENTION

The present invention provides, according to some embodiments, human implantable tissue expanders comprising an inner foam filling enclosed within an expansion restricting layer that can be made of substantially non-stretchable mesh or a sheet of material, and further within a shell composed of one or more layers. The foam filling is typically closed-cell foam. Upon changes of surrounding pressure, for example at low ambient pressure, a foam filling may expand and its shape and volume may be altered. Tissue expanders according to embodiments of the present invention comprise a substantially non-stretchable layer that is configured to prevent such undesired expansion. In addition, tissue expanders according to embodiments of the present invention comprise several features intended to confer natural tactility to the implant. The tissue expanders disclosed herein may find use in the augmentation and/or reconstruction of various soft tissues, including breast, pectorals, calf muscles etc.

According to one aspect, the present invention provides a human implantable tissue expander comprising: an inner foam filling; a substantially non-stretchable, resilient, expansion restricting layer configured to retain a volume of said foam filling upon changes of ambient pressure, temperature or both; and a sealing shell comprising one or more layers formed of a resilient material.

In some embodiments, the inner foam filling is enclosed within the substantially non-stretchable, resilient, expansion restricting layer, and the sealing shell is an outer shell surrounding said substantially non-stretchable, resilient, expansion restricting layer.

In other embodiments, the inner foam filling is enclosed within the sealing shell, and the substantially non-stretchable, resilient, expansion restricting layer is an outer layer surrounding said sealing shell.

In some embodiments, the tissue expander is substantially devoid of a lubricating material. In particular, in some embodiments, the one or more layers of the sealing shell are substantially devoid of a lubricant coating.

In some preferred embodiments, the inner foam filling comprises closed-cell foam.

In some embodiments, the inner foam filling comprises a single foam element.

In some embodiments, the inner foam filling comprises a plurality of foam elements. In some embodiments, the tissue expander comprises a plurality of foam elements, each enclosed within a substantially non-stretchable resilient expansion restricting layer.

In some embodiments, the tissue expander comprises a plurality of foam elements, wherein at least some of said plurality of foam elements are collectively enclosed within a single substantially non-stretchable resilient expansion restricting layer. In some embodiments, the tissue expander comprises a plurality of foam elements, all collectively enclosed within a single substantially non-stretchable resilient expansion restricting layer.

In some embodiments, the substantially non-stretchable resilient expansion restricting layer constitutes a distinct layer. In other embodiments, the substantially non-stretchable resilient expansion restricting layer is at least partially embedded in said sealing shell.

In some embodiments, the tissue expander further comprises a flexible sealed enclosure, enclosing said foam filling. In some embodiments, the flexible sealed enclosure is the immediate layer enclosing said foam filling, and the substantially non-stretchable resilient expansion restricting layer is a distinct layer overlaying said flexible sealed enclosure. In other embodiments, the substantially non-stretchable resilient expansion restricting layer is at least partially embedded in said flexible sealed enclosure.

In some embodiments, the substantially non-stretchable resilient expansion restricting layer comprises a plurality of substantially non-stretchable resilient expansion restricting layers.

In some embodiments, the sealing shell comprises a first layer configured to define the consistency and tactility of the sealing shell, and a second layer overlaying said first layer and configured to define the mechanical properties of said sealing shell.

In some embodiments, the one or more layers of said sealing shell are of uniform thickness.

In some embodiments, the one or more layers of said sealing shell are of varying thickness.

In some embodiments, the tissue expander further comprises an internal skeleton element.

In some embodiments, the internal skeleton element comprises an array of elongated cells extending longitudinally between a base surface and an outer surface along mutually parallel axes and being defined by elongate cell walls formed of a resilient material.

In some embodiments, the elongated cells fully extend between opposing surfaces of the tissue expander. In other embodiments, the elongated cells partially extend between opposing surfaces of the tissue expander.

In some embodiments, the inner foam filling substantially fills said elongated cells.

In some embodiments, the inner foam filling extends outside the base surface, the outer surface or both of said array of elongated cells.

In some embodiments, the internal skeleton element comprises one or more flexible tubes.

In some embodiments, the inner foam filling substantially fills said one or more flexible tubes.

In some embodiments, the inner foam filling further fills voids among folds of the flexible tubes, and between an outer wall of a tube and an inner wall of the tissue expander.

In some embodiments, the substantially non-stretchable resilient expansion restricting layer further comprises one or more joining means, such as sutures, glue or both, configured to retain a shape and volume of said inner foam filling upon changes of ambient pressure, temperature or both.

In some embodiments, the tissue expander further comprises an outer mesh partially covering an outermost layer of the tissue expander.

In some embodiments, the outer mesh comprises a single mesh patch.

In some embodiments, the outer mesh comprises a plurality of mesh patches.

In some embodiments, the tissue expander further comprises a balloon configured to inflate upon introduction of liquid, gas or a combination thereof into an interior thereof, and deflate upon removal of liquid, gas or a combination thereof from said interior thereof.

In some embodiments, the balloon is external to an outermost layer of the tissue expander.

In some embodiments, the external balloon is a distinct compartment attached to an outermost layer of the tissue expander.

In some embodiments, the external balloon shares a common wall with an outermost layer of the tissue expander.

In some embodiments, the balloon is internal to an innermost layer enclosing said foam filling.

In some embodiments, the internal balloon is a distinct compartment embedded within the inner foam filling, unattached to an innermost layer enclosing said foam filling.

In some embodiments, the internal balloon is a distinct compartment embedded within the inner foam filling and attached to an innermost layer enclosing said foam filling.

In some embodiments, the internal balloon shares a common wall with an innermost layer enclosing said foam filling.

In some embodiments, the internal balloon is between said substantially non-stretchable resilient expansion-restriction layer and an innermost layer of said outer sealing shell.

In some embodiments, a tissue expander comprising a balloon further comprises a tube communicating with the interior of the balloon.

In some embodiments, a tissue expander comprising a balloon further comprises a valve communicating with the interior of the balloon. The valve according to embodiments of the present invention is configured to permit fluids to flow therethrough when in an open position, and substantially block fluid flow therethrough when in a closed position. When in a closed position, the valve is configured to maintain the balloon sealed.

In some embodiments, the valve is an integrated valve in the sealing shell, communicating with the interior of the balloon.

In some embodiments, the tissue expander comprises a balloon, a tube communicating with the interior of the balloon, and a valve connecting between the balloon and tube, wherein the valve is configured to allow passage of fluids between the tube and balloon when in an open position, and substantially block passage of fluids between the tube and balloon when in a closed position.

In some typical embodiments, the valve is a self-sealing valve.

In some embodiment, the tissue expander comprises a device (e.g., a plate) with an identifying code configured for non-invasive identification of said tissue expander when implanted in a subject.

In some embodiments, a human implantable tissue expander is provided, the tissue expander comprising: an inner foam filling enclosed within a flexible sealed enclosure; a substantially non-stretchable resilient expansion restricting layer at least partially embedded in said flexible sealed enclosure; and an outer sealed shell comprising one or more layers formed of a resilient material.

These and further aspects and features of the present invention will become apparent from the figures, detailed description and claims which follow.

DETAILED DESCRIPTION OF THE INVENTION

The present invention is directed to human implantable tissue expanders.

Figure 1:
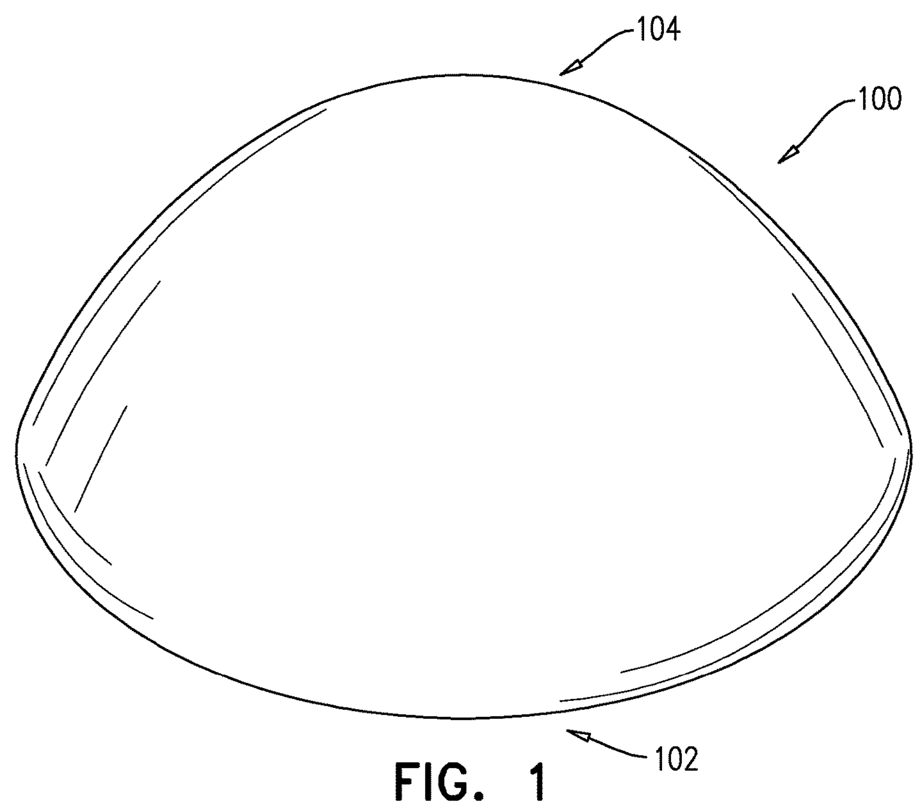
FIG. 1. A perspective view illustration of a tissue expander according to some embodiments of the present invention.

FIG. 1 illustrates a perspective view of a tissue expander (100) according to some embodiments of the present invention, suitable, for example, for breast augmentation and/or reconstruction. The tissue expanders according to embodiments of the present invention are sized and shaped in accordance with their intended location in the human body. As illustrated in FIG. 1, in some embodiments, the implant comprises a generally flat surface (102) at one side thereof, and a generally convex surface (104) at another, opposing, side thereof.

A tissue implant according to embodiments of the present invention is preferably resiliently deformable and compressible, and can be deformed or compressed to a deformed, compressed shape in which it has a substantially reduced minimum dimension, thereby permitting insertion of the implant through an aperture in a cutaneous layer when the implant is in the deformed, compressed shape, and allowing the implant, by virtue of its resiliency and ability to decompress, to regain a desired original three dimensional shape when placed at a desired location within the body for augmentation or reconstruction of the desired three dimensional shape of a body portion.

Figure 2A:
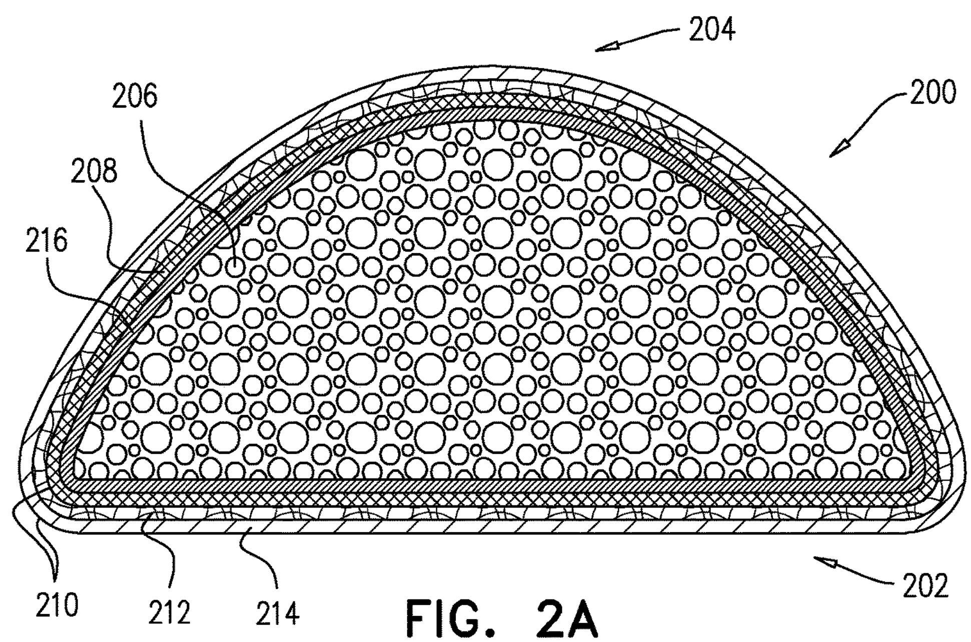
FIG. 2A-2D. Cross-sectional illustrations of tissue expanders according to some embodiments of the present invention.

FIGS. 2A-2D illustrate cross-sectional side views of tissue expanders (200) according to some embodiments of the present invention, suitable, for example, for breast augmentation and/or reconstruction. FIG. 2A shows a tissue expander (200) comprising a flat base surface (202) and a convex outer surface (204). The tissue expander (200) has an inner volume filled with a foam filling (206) and defined by a substantially non-stretchable, resilient expansion restricting layer (208), such as mesh, enclosing the foam filling.

As used herein, the phrases "substantially non-stretchable expansion restricting layer", "substantially non-expandable expansion restricting layer" or simply "expansion restricting layer", refer to a layer, such as a mesh, that does not stretch or expand, namely elongate in any direction or allow an increase in volume, to more than about 10% relative to its initial length or volume, preferably the expansion restricting layer does not stretch or expand to more than about 1-5% relative to its initial surface area and preferably the expansion restricting layer does not stretch or expand at all under pressure changes of about −0.9 atmosphere. The expansion restricting layer defines a fixed surface area of the foam body of the implant, preventing the expansion of the gas in the foam-body under negative pressure changes. According to some embodiments, the term "fixed" surface area may refer to a constant or substantially constant surface area.

The expansion restricting layer according to embodiments of the present invention is formed of a biocompatible material, such as polyester, polyethylene, polyamide, Gortex®, cellophane, aluminum foil or others known to be used for implantation in the human body.

The expansion restricting layer may be a woven fabric, a non-woven fabric, a knitted fabric or a sheet of material or a combination of such. The expansion restricting layer may be formed of two substantially non-expandable sheets joined together. The expansion restricting sheet may be meshed. A knitted or woven layer may be characterized by the thickness of the layer being uniform or varied, and also by varied or uniform pore size, thread thickness and type of threads. The expansion restricting layer may be formed of a single piece, or multiple pieces or strands of material in any suitable manner, including for example, weaving, injection molding, extruding, winding or wrapping. The expansion restricting layer may be closed to create a sealed enclosure by sewing, ultrasonic welding, gluing or other techniques known in the art.

In some embodiments, the expansion restricting layer is pre-formed, the foam filling is inserted inside the preformed expansion restricting layer, and the edges of the expansion restricting layer are then sealed to form a sealed expansion restricting layer enclosing the foam filling. In other embodiments, the expansion restricting layer is formed as an outer layer of the filling.

The expansion restricting layer has typically lower elongation capability and higher tensile strength capability compared to the other layers/enclosures that constitute the tissue expander according to embodiments of the present invention. In some embodiments, the expansion restricting layer is composed of a plurality of layers. For example, a mesh may compose a plurality of mesh layers.

The foam filling according to some embodiments of the present invention is a matrix characterized by a closed-cell structure filled with gas, for example, air-filled foam. The foam filling can be produced by methods known in the art, for example, by mixing at room temperature two different biocompatible polymers, e.g. silicones, that release gas (e.g., hydrogen, oxygen or ammonia) in an exothermic reaction upon mixing thereof. The generated gas is trapped within the silicone and generates closed-cell foam upon curing, meaning that each pocket of gas is completely surrounded by solid material. The gas is replaced spontaneously by air until partial gas pressure equilibrium is reached. Part of the outer layer of the foam may include open cells. Additionally, in order to change the consistency of the foam body filling the implant, the cured foam body or several elements of the foam body may undergo pressure modification, e.g. weight milling that causes the transformation of some of the closed cells into open cells, thus softening the consistency of the foam body. The density of the foam filling when filled with gas is generally less than about 0.5 gram per cubic centimeter and preferably less than about 0.3 gram per cubic centimeter. Pore size and number of cells per unit volume are typically defined by manufacturing parameters, such as the curing temperature and ambient pressure, and can vary according to the desired weight and consistency of the foam filling.

The foam filling has a defined shape that corresponds to its intended location within the body. The foam filling can be manufactured by molding, cutting partial volumes from a larger foam lump and joining them together, or extrusion. For example, a foam filling can be prepared by mixing two parts of uncured silicone generating gas by a gas forming reaction, filling or injecting the dispersion into a mold and allowing it to cure at room temperature. The size of the cells or pores can be controlled by changing pressure within the mold at various pressure differences and various time frames, where higher pressure results in the formation of smaller cells. The size of the cells can also be controlled by changing the temperature of the mold, where higher temperatures result in the formation of larger cells.

The illustrated foam filling (206) is shaped to include a flat base surface and a convex outer surface. The expansion restricting layer (208) is configured to minimize configurational changes of the foam filling, or retain the volume of the foam filling, due to changes of the internal pressure of the gas inside the foam cells, upon changes in the ambient pressure, temperature or both. For example, the expansion restricting layer is configured to prevent an undesired expansion of the foam filling upon a decrease of ambient pressure. The foam filling (206) illustrated in FIG. 2A comprises a single foam element that substantially fills the inner volume of the tissue expander. In alternative embodiments, exemplified in FIG. 2D, the foam filling is composed of a plurality of separate foam elements (206*a-d*), that collectively fill the inner volume of the tissue expander. In the embodiment illustrated in FIG. 2D, the plurality of foam elements are enclosed within a single expansion restriction layer (208). In other embodiments, the tissue expander comprises a plurality of expansion restricting layers, each enclosing a single foam element out of the plurality of foam elements. In additional embodiments, some or all of the foam elements are glued or joined together.

The tissue expander (200) further comprises an elastomeric sealing shell (210). In the illustrated embodiment, the shell is an outer layer overlaying the expansion restricting layer (and foam filling). In other embodiments, the foam filling is enclosed within the sealing shell, and the expansion restricting layer is the outer layer, surrounding the sealing shell. Thus, the expansion restricting layer according to embodiments of the present invention may constitute an outer layer or an intermediate layer.

The illustrated shell is sealed and completely encloses the foam filling (206) and expansion restricting layer (208). The illustrated shell (210) is composed of first (212) and second (214) layers, wherein the first layer defines the consistency and tactility of the shell and the second layer defines the mechanical properties of the shell. Each layer may have a uniform or varied thickness. In some embodiments, exemplified in FIG. 2E that shows a perspective view of a tissue expander (200), the external surface of the first (outer) layer has a plurality of grooves (220) constructed therein in the manufacturing process, which may have different dimensions. Such grooves are advantageous, for example, when the shell is constructed by over molding the layers in an inverse order, where the outer layer is molded first, and the subsequent inner layers are molded over the outer layer. The grooves allow the outer layer to form the exact desired shape upon inversion of the resulting shell. The layers may have the same or different thickness. The number of layers and their characteristics (such as the polymers the layers are made of), typically define the consistency and tactility of the shell, and consequently the consistency and tactility of the tissue expander.

The illustrated tissue expander (200) further comprises a flexible sealed enclosure (216) located between the expansion restricting layer (208) and foam filling (206), enclosing the foam filling.

The expansion restricting layer (208) illustrated in FIG. 2A constitutes a distinct layer overlaying the flexible sealed enclosure (216) and foam filling (206), and underlying the shell (210). In alternative embodiments, the expansion restricting layer is wholly or partially embedded in the flexible sealed enclosure. Embedding the expansion restricting layer in the flexible sealed enclosure may improve the consistency and tactility of the tissue implant by softening its touch. In additional embodiments, the expansion restricting layer is wholly or partially embedded in the shell, typically in the innermost layer of the shell. In some embodiments, an expansion restricting layer that constitutes a separate layer is embedded in a biocompatible polymer such as silicone.

When the expansion restriction layer constitutes a distinct layer (rather than embedded in the flexible sealed enclosure or in one of the layers of the outer shell), it may be affixed (for example, glued) to its immediate underlying and/or overlying layer. For gluing the expansion restricting layer to an underlying layer, the expansion restricting layer can be manufactured to enable the passage of glue through the mesh pores.

Figure 2B:
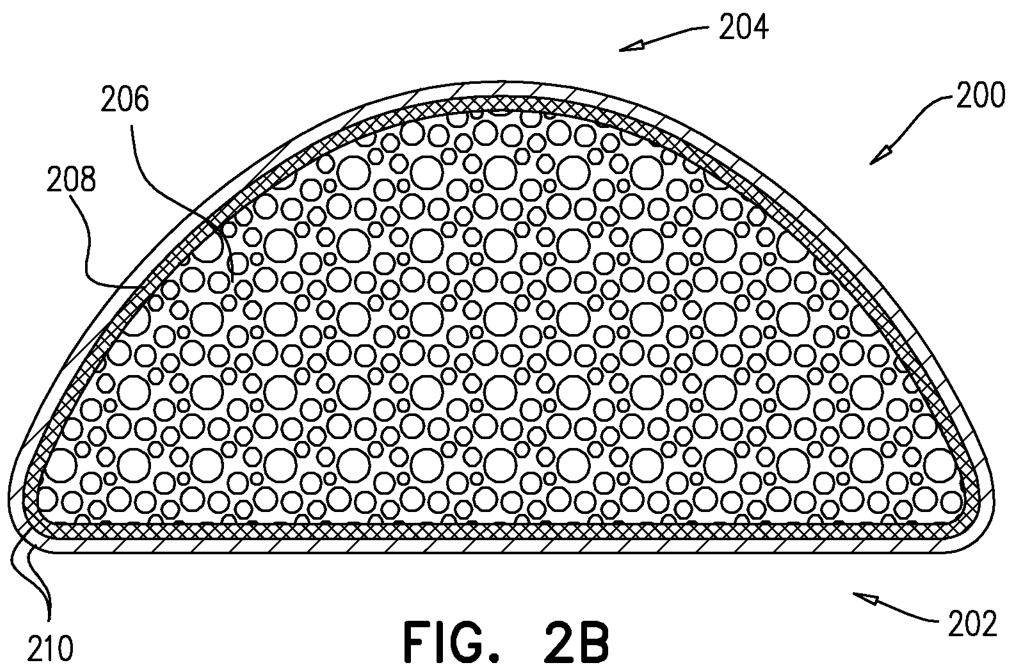

An alternative configuration is illustrated in FIG. 2B, which shows a tissue expander (200) comprising a foam filling (206), an expansion restricting layer (208) enclosing the foam filling, and a shell (210) composed of a single layer. The foam filling (206) is confined within an expansion restricting layer envelope, without an intervening layer (or enclosure) between them.

Figure 2C:
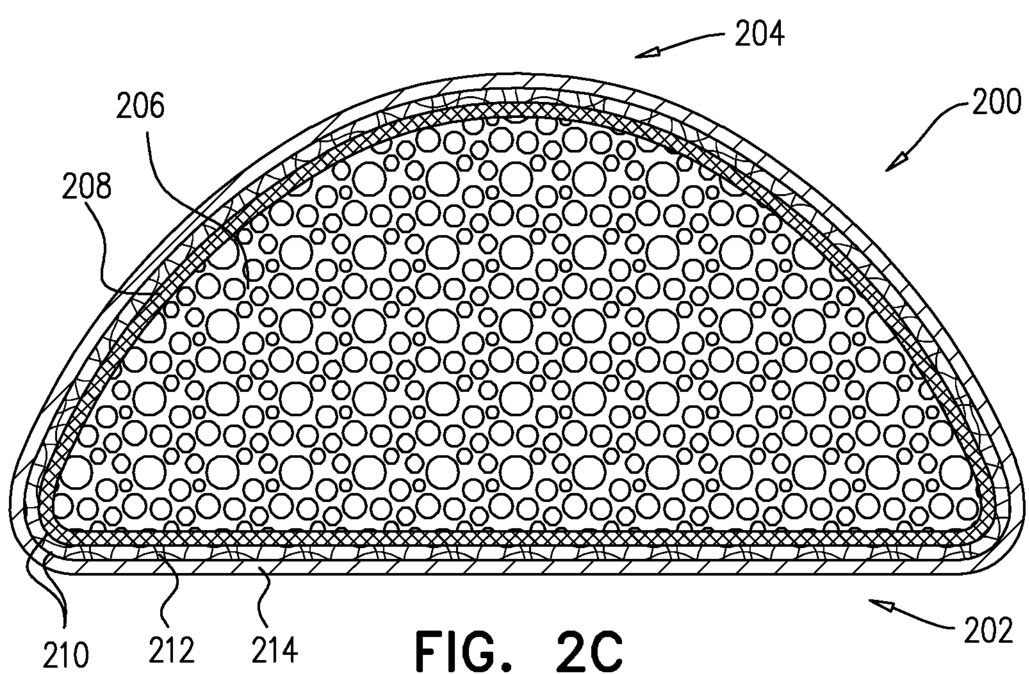
Figure 2D:
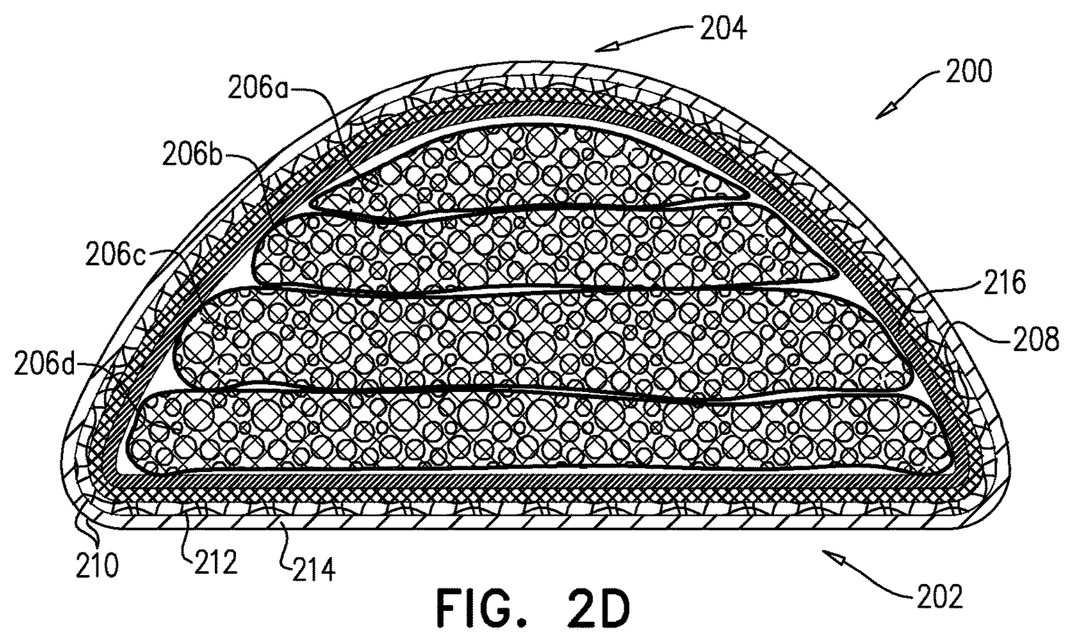
Figure 2E:
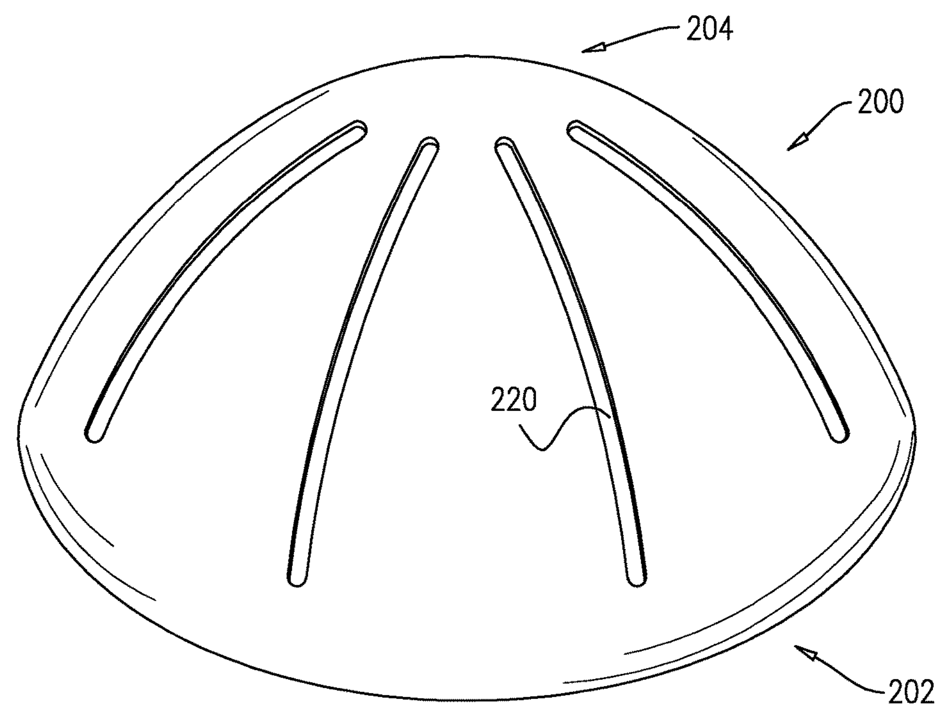
FIG. 2E. A perspective view illustration of a tissue expander according to some embodiments of the present invention.

Another alternative configuration is illustrated in FIG. 2C, which shows a tissue expander (200) comprising a foam filling (206), an expansion restricting layer (208) enclosing the foam filling, and a shell (210) composed of two layers (212, 214). The foam filling (206) is confined within an expansion restricting envelope, without an intervening layer (or enclosure) between them.

A foam filling, an expansion restricting layer surrounding the foam filling and an optional flexible sealed enclosure can be collectively referred to as the core of the tissue expander, according to some embodiments of the present invention. In some embodiments, the core is covered by an outer shell comprising one or more layers, and fills substantially the entire volume of the outer shell. The core may include a skeleton element, as will be further described below.

The layers of the outer shell, as well as the flexible sealed enclosure, are typically formed of biocompatible, resilient materials, such as silicone, and manufactured by molding. Manufacturing of the outer shell may be performed by a single-layer molding of each layer independently, followed by joining (for example gluing) the layers together. Alternatively, over-molding may be performed, where successive layers are molded one on top of the other. Dip molding using pre-formed mandrels can be used for manufacturing the outer shell, by serial dipping steps to form the layers that constitute the shell. In addition, a combination of the above methods may be used. In some embodiments, the outermost layer of the shell is molded first, and the inner layer(s) are molded over the external layer. The resulting shell is then turned inside out and laid over the core containing the foam filling, expansion restriction layer (e.g., a mesh) and optionally one or more flexible sealed enclosures. The different components of the tissue expander may be formed of the same or different materials.

Varying thicknesses of the layers that constitute the outer shell and every other layer or structure of the implant according to embodiments of the present invention can be facilitated by transfer/compression/injection molding or any other technique using molds for manufacturing.

Figure 2F:
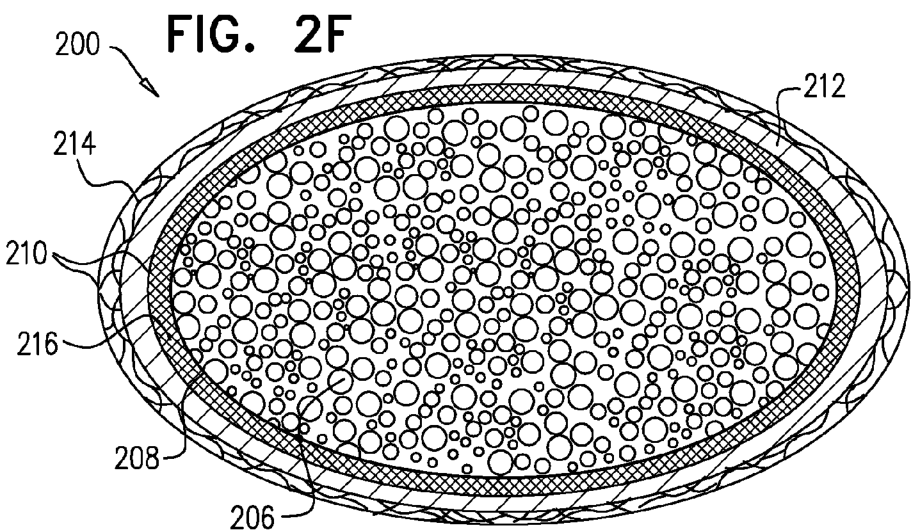
FIG. 2F. A cross-sectional illustration of a tissue expander according to some embodiments of the present invention.
Figure 2G:
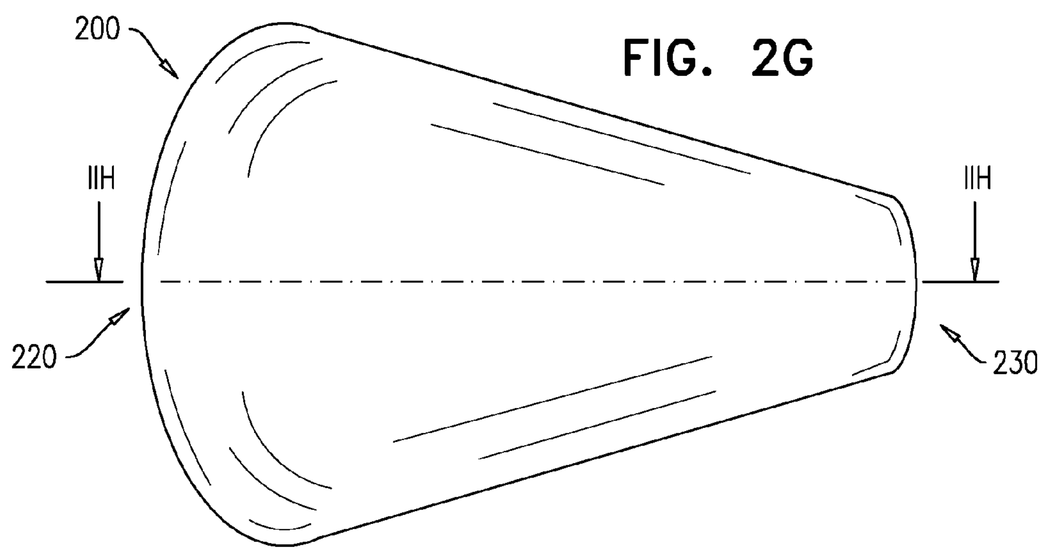
FIGS. 2G-2H. Top view and cross-sectional illustrations of a tissue expander according to some embodiments of the present invention.
Figure 2H:
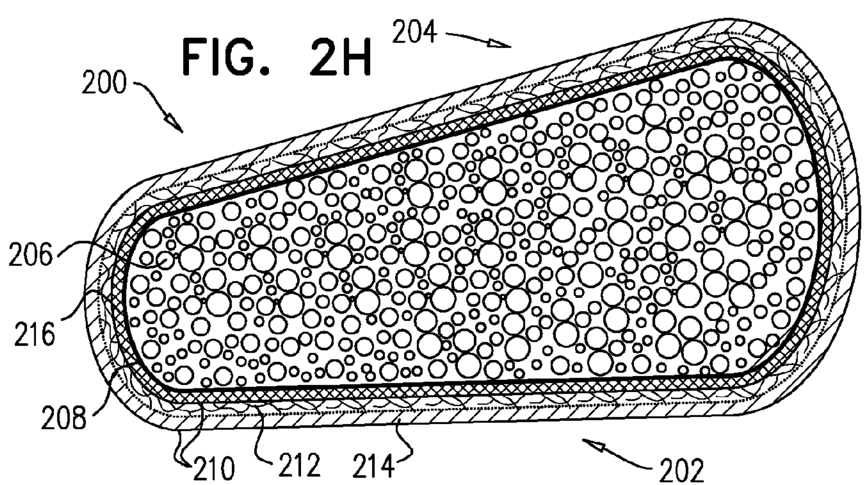

FIGS. 2F-2H illustrates alternative configurations of an implantable tissue expander according to embodiments of the present invention.

FIG. 2F illustrates a cross-sectional view of a tissue expander (200) characterized by an egg-shaped three-dimensional configuration, suitable, for example, for lumpectomy procedures. In the illustrated embodiment, the tissue expander (200) comprises an inner foam filling (206) enclosed within a flexible sealed enclosure (216) having an expansion restricting layer (208) embedded therein. The illustrated tissue expander (200) further comprises an outer shell (210) composed of first (212) and second (214) layers. In some embodiments, the external surface of second layer (214) is textured. In some embodiments, first layer (212) is characterized by a softer consistency compared to second layer (214).

FIGS. 2G-2H illustrate a tissue expander characterized by a wedge-shaped three-dimensional configuration, suitable, for example, for segmentectomy/quadrantectomy procedures.

FIG. 2G is a top view of the wedge-shaped tissue expander (200). When viewed from the top, the illustrated tissue expander (200) comprises a first (220) and second (230) arcs at opposing ends thereof, wherein first arc (220) has greater width than second arc (230).

FIG. 2H is a cross-sectional view of the wedge-shaped tissue expander (200) across line IIH-IIH of FIG. 2G. When viewed from the side, the illustrated tissue expander (200)

comprises a generally flat posterior surface (202), intended to face the chest wall and a contoured anterior surface (204), intended to face an overlaying breast tissue. The side view of the illustrated tissue expander follows the natural silhouette of the female breast, which slopes downwards to form a fuller projection at its lower part. Contoured anterior surface (204) forms a slope such that one end of the tissue expander has greater thickness than the opposing end thereof. Tissue expander (200) comprises an inner foam filling (206) enclosed within a flexible sealed enclosure (216) having an expansion restricting layer (208) embedded therein. The illustrated tissue expander (200) further comprises an outer shell (210) composed of first (212) and second (214) layers.

The tissue expanders according to embodiments of the present invention may comprise one or more internal skeleton elements.

The term "skeleton element" is used throughout to refer to an element which provides structural support and optionally defines a predetermined three-dimensional shape of the tissue implant.

Figure 3A:
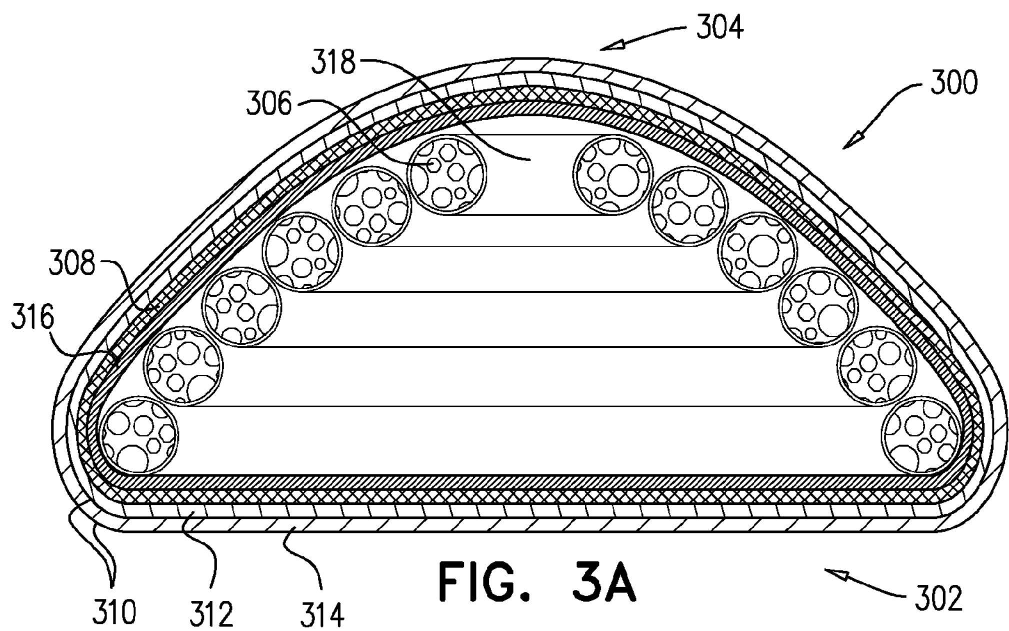
FIGS. 3A-3B. Cross-sectional and cutaway top view illustrations of a tissue expander according to some embodiments of the present invention.
Figure 3B:
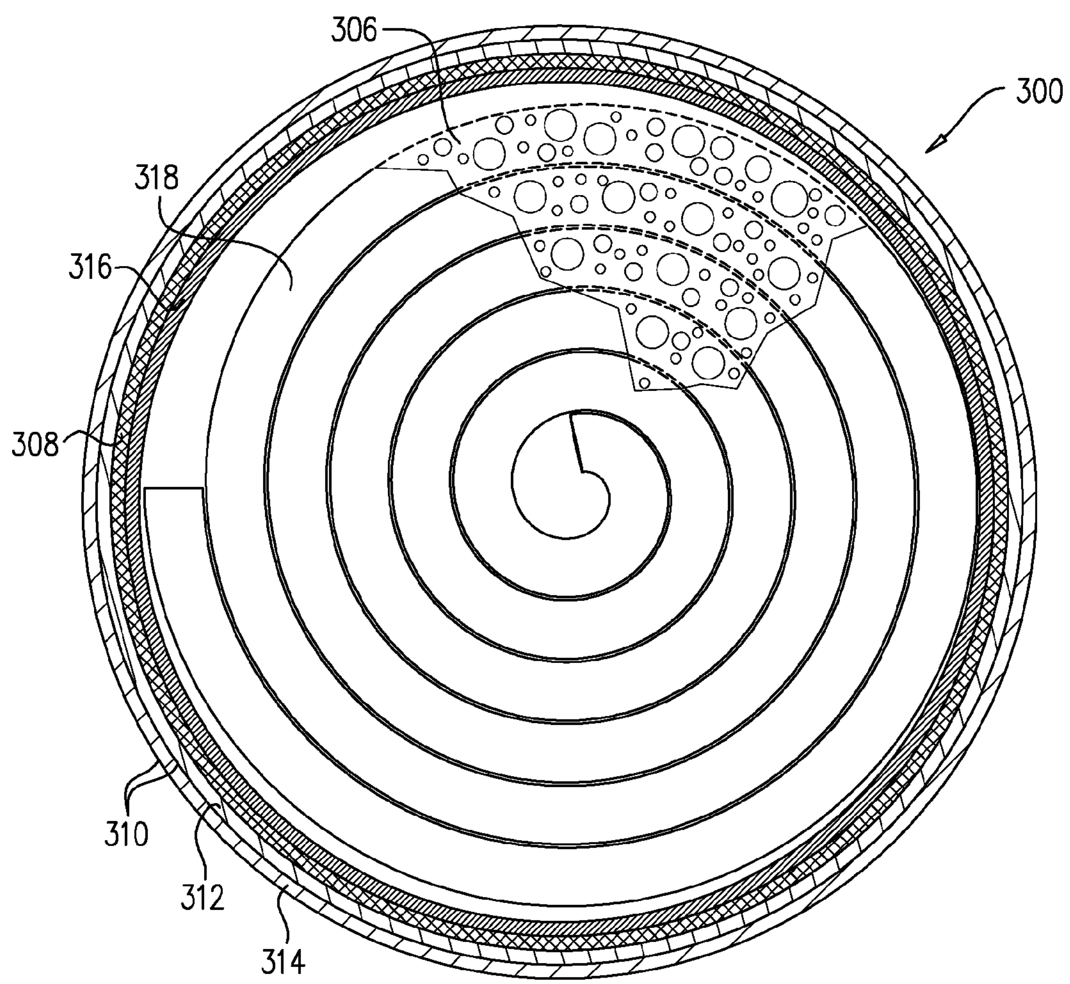

FIGS. 3A-3B respectively illustrate a cross-sectional side view and a cutaway top view of a tissue expander (300) according to some embodiments of the present invention, suitable, for example, for breast augmentation and/or reconstruction. FIGS. 3A-3B show a tissue expander (300) as illustrated in FIG. 2A, that further comprises an internal skeleton element in the form of a folded tube (318) formed of a resilient material, such as soft silicone or polyurethane. Typically, the tube is hollow and contains therein the foam filling. The foam filling substantially fills the tube, meaning that it occupies substantially the entire inner volume of the tube. In some embodiments, the tube has a polygonal cross-section. In particular embodiments, the tube has a hexagonal cross-section. FIGS. 3A-3B illustrate partial sections of the hollow tube showing the foam filling (306) in the tube. Preferably, the foam filling is confined within the tube and substantially fills the tube. In some embodiments, the foam material also surrounds the tube such that it occupies voids formed between the folds of the tube or between the external wall of the tube and an outer enclosure or mesh. The diameter of the tube may be constant or varied along its length. The thickness of the tube wall may be constant or varied along its length.

The illustrated tissue expander (300) comprises a flat base surface (302) and a convex outer surface (304). The tissue expander (300) comprises an inner foam filling (306) within a helical tube (318). The helical tube is folded so as to create an overall conical structure that conforms to the shape and design of the tissue expander (300). The foam filling and tube are enclosed within a flexible sealed enclosure (316), and further within a non-stretchable, resilient expansion restricting layer (308). The tissue expander (300) further comprises an outer shell (310) comprising two layers (312, 314).

Figure 4A:
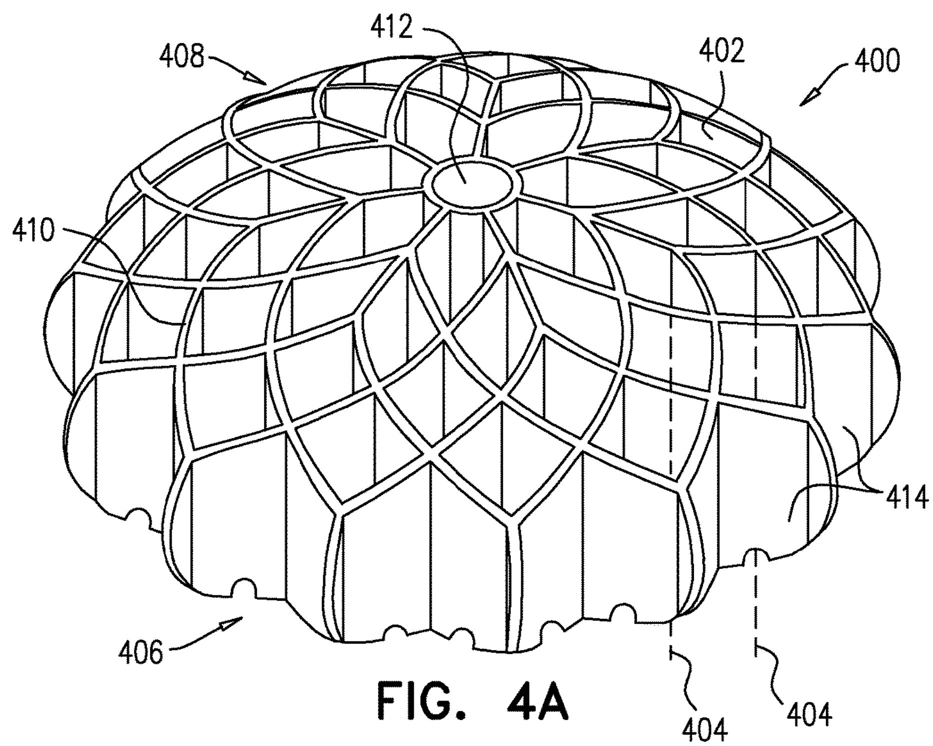
FIGS. 4A-4B. Perspective view illustrations of skeleton elements according to some embodiments of the present invention.
Figure 4B:
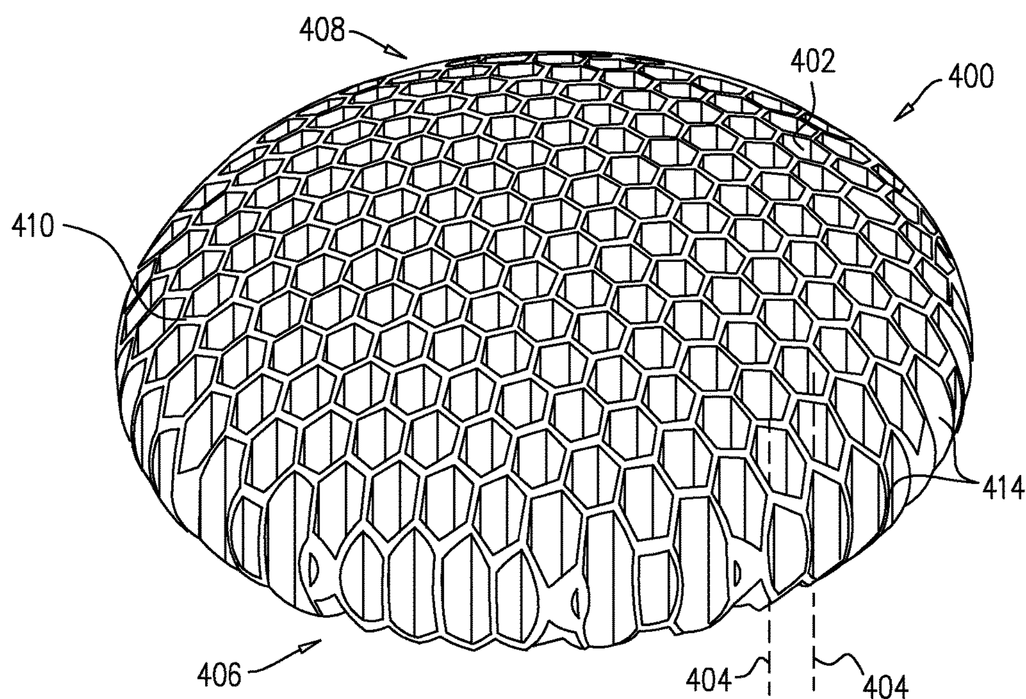

FIGS. 4A-4B illustrate alternative forms of skeleton elements that may be contained within a tissue expander according to some embodiments of the present invention.

FIG. 4A is a perspective view of a resiliently deformable skeleton element (400) that includes an array of elongate cells (402) extending along mutually generally parallel axes (404) from an imaginary flat base surface (406) to an imaginary convex outer surface (408) that is tucked in adjacent the imaginary base surface (406). Elongate cells (402) are mutually defined by elongate cell walls (410) formed of a resilient material. In the illustrated embodiment, the array of elongate cells (402) is characterized in that it includes a central cylindrical cell (412) and that elongate cell walls (410) are of generally uniform thickness. It is also characterized in that a regular pattern of partial cells (414) are located along the periphery of the array. In the illustrated embodiment, all of the partial cells (414) are identical. In alternative embodiments, this is not necessarily the case. In yet additional alternative embodiments, the elongate cell walls (410) need not be of generally uniform thickness and may be of different thicknesses and/or varying thickness.

FIG. 4B is a perspective view of a resiliently deformable skeleton element (400) that includes an array of identical elongated cells (402), each having an hexagonal cross section, extending along mutually generally parallel axes (404) from an imaginary flat base surface (406) to an imaginary convex outer surface (408), which is tucked in adjacent the imaginary base surface (406). Elongate cells (402) are mutually defined by elongate cell walls (410) formed of a resilient material. In the illustrated embodiment, the array of elongate cells (402) is preferably characterized in that elongate cell walls (410) are of generally uniform thickness. It is also characterized in that a regular pattern of partial cells (414) are located along the periphery of the array. In the illustrated embodiment, the partial cells (414) are not identical.

Figure 4C:
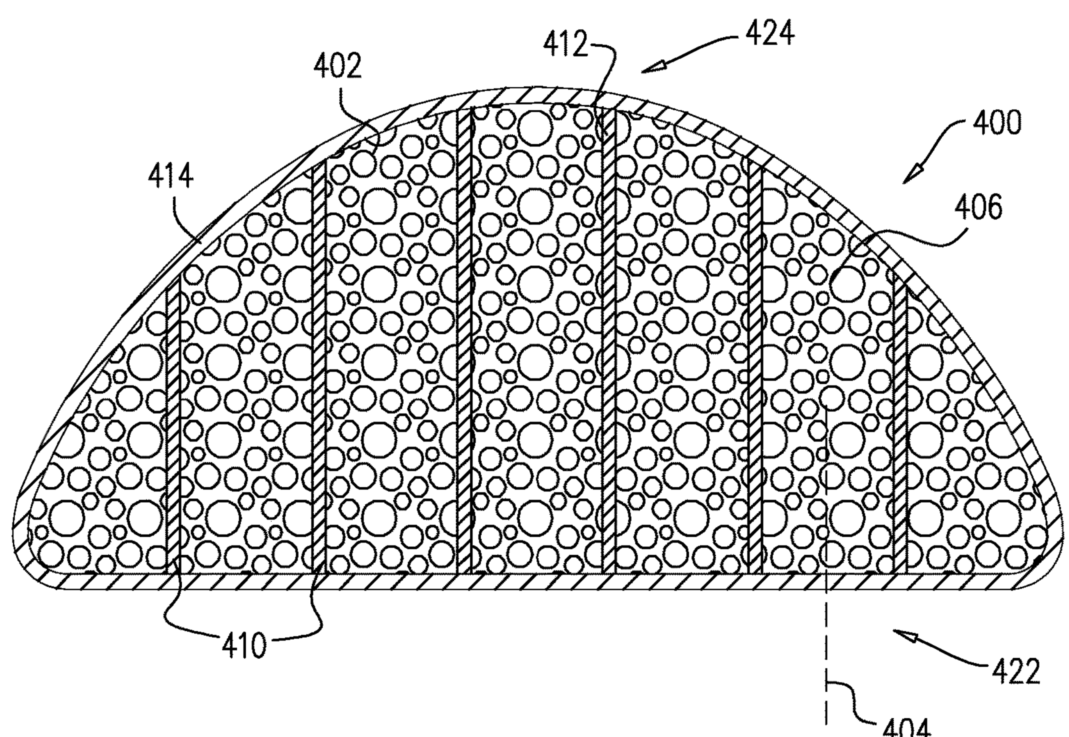
FIG. 4C. Cross-sectional illustration of a tissue expander according to some embodiments of the present invention.

FIG. 4C is a cross-sectional side view of a tissue expander (400) according to some embodiments of the present invention, comprising an internal skeleton element in the form of an array of elongated cells, for example a skeleton element as shown in FIGS. 4A-B. As seen in FIG. 4C, the illustrated tissue expander (400) comprises a flat base surface (422) and a convex outer surface (424). The tissue expander comprises an array of elongate cells (402) extending along mutually generally parallel axes (404), defined by elongated cell walls (410) formed of a resilient material.

In the illustrated embodiment, the elongated cells fully extend between the base (422) and outer (424) surfaces of the tissue expander, such that substantially all the edges (412) of the cell walls are in contact with the innermost layer (414) enclosing the foam filling (406). For simplicity, FIG. 4C presents only the innermost layer enclosing the foam, which is, for example, a flexible sealed enclosure or an expansion restricting layer. It is appreciated that the tissue expander includes additional layers, such as the layers that constitute the sealing shell. In the illustrated embodiment, the foam filling (406) substantially fills all the cells of the skeleton element. In alternative embodiments, the foam filling fills only some of the cells. The volume and amount of foam within each cell can vary among the cells.

In alternative embodiments, the elongated cells partially extend between the base and outer surfaces of the implantable tissue expander, such that only some (or none) of the edges of the cell walls are in contact with the innermost layer enclosing the foam filling. According to these embodiments, the foam filling may fill the cells and further extend outside the cells, to fill voids between the skeleton element and an inner wall of the tissue expander.

Thus, in some embodiments, the foam filling fills the cells defined by the cell walls and further extends outside the base surface and/or outer surface of the array of elongated cells, thus softening the touch of an implant containing a skeleton element.

The internal skeletal element may be formed of the same or different material as the other components of the tissue expander.

Additional types of skeleton elements, as well as methods for their production, are described, for example, in WO 2007/000756, WO 2008/081439 and WO 2010/049926.

Figure 5A:
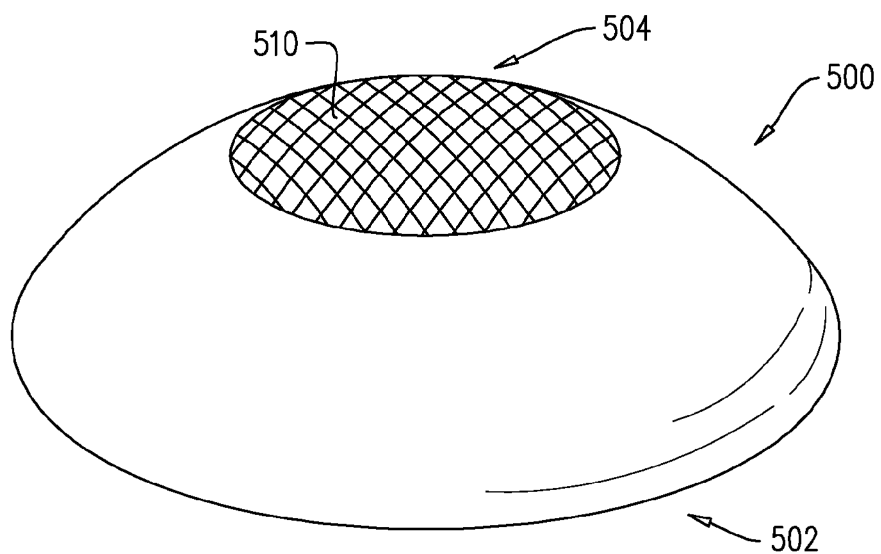
FIGS. 5A-5B. Perspective and top view illustrations of a tissue expander to some embodiments of the present invention.
Figure 5B:
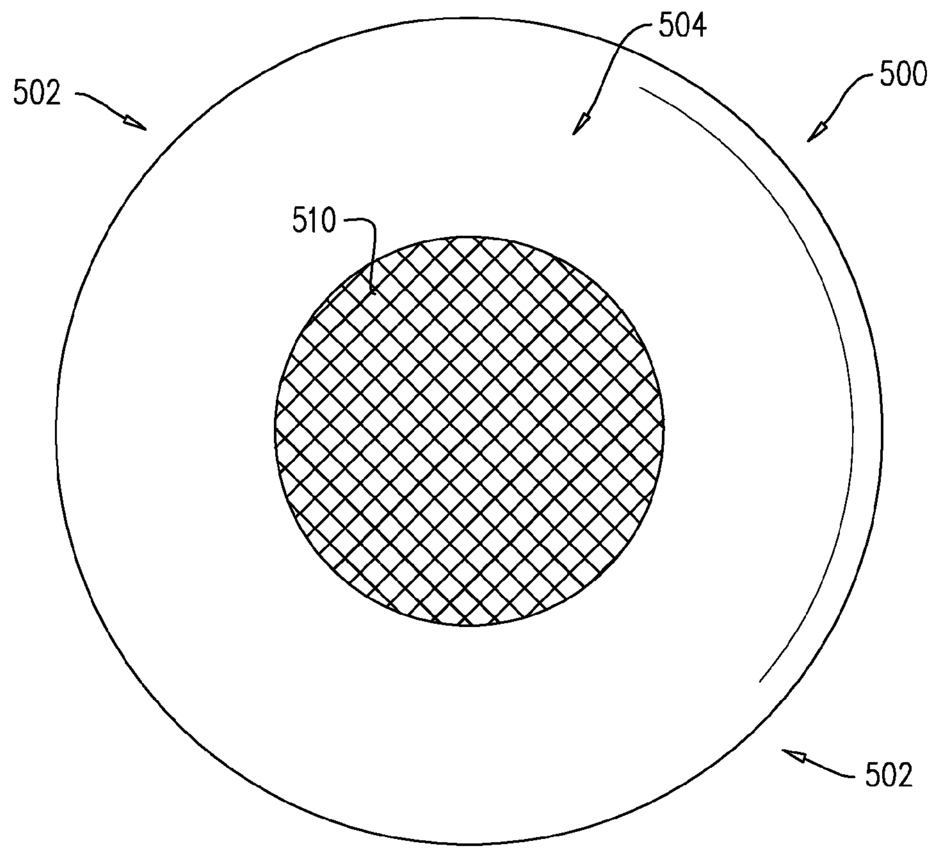

FIGS. 5A-5B respectively illustrate a perspective view and a top view of a tissue expander (500) according to some embodiments of the present invention, suitable, for example, for breast augmentation and/or reconstruction. FIGS. 5A-5B show a tissue expander (500) of the present invention that comprises an outer mesh (510) partially covering the external surface of the tissue expander. The external surface of a tissue expander according to embodiments of the present invention is typically the outermost layer of the outer shell of the tissue expander.

The illustrated tissue expander (500) comprises a flat base surface (502) intended to face the chest wall, and a convex outer surface (504) intended to face breast tissue. In the illustrated embodiment, the tissue expander comprises a single mesh patch (510) at the apex of the convex surface of the tissue expander. In alternative embodiments, the outer mesh comprises a plurality of mesh patches, at different positions on the external surface of the tissue expander and of different patch size, patch thickness and pore size. The outer mesh may be knitted or woven or made of a complete or meshed sheet, and made from a biocompatible material like polyester or polyamide for instance.

Following implantation of a tissue expander, connective tissue slowly grows and surrounds the tissue expander. The presence of patches of mesh on the external surface of the tissue expander facilitates tissue ingrowth into the pores of the mesh, eventually forming a tissue-implant complex that anchors the implant to the surrounding tissues.

In a breast implant for example, an anterior mesh patch, on the convex surface thereof, will anchor the implant to the overlaying breast tissue, thus creating a new implant-breast tissue complex that acts as a single unit against external forces applied thereto, and mimics a natural breast to a great extent. A posterior mesh patch, on the flat surface thereof, will anchor the implant to the chest wall, and is likely to mimic the natural breast to a lesser extent.

The tissue expanders according to embodiments of the present invention may comprise one or more balloons.

The term "balloon" is used throughout to refer to a flexible, sealed enclosure configured for controlled inflation and deflation, particularly after implantation of the tissue expander. The balloon is being inflatable upon introduction of liquid or gas into an interior thereof, and deflatbale upon removal of liquid or gas from said interior thereof. In some embodiments, the balloon is an external balloon attached to the outermost layer of the implant. In other embodiments, the balloon is internal. In some embodiments, an internal balloon is embedded within the foam filling. In other embodiments, an internal balloon is outside the foam filling, for example between an expansion-restriction layer and an outer shell, attached to the inner surface of the shell.

The balloon is typically associated with a port enabling communication to the interior of the balloon for inflation and or deflation. There are many ports known and described in the literature and one example for a port is an integrated valve mechanism comprising a port integrated, for example, in the shell of the implantable tissue expander and accessed by a needle through the skin. Another example is a remote valve mechanism comprising a tube communicating with the interior of the balloon and protruding from the tissue expander such that it is accessible to a surgeon after the tissue expander is inserted into a subject. The tube is preferably connected to the balloon via a self-sealing valve that is incorporated into the wall of the balloon and configured to maintain the balloon sealed after the removal of the tube. The tube and valve may facilitate the introduction, or injection, of a filling, such as liquid, gas or a combination thereof, into the balloon, or removal of the filling of the balloon from its interior.

Before implantation in a subject, the balloon is preferably in a collapsed, deflated form. The implantable tissue expander comprising the deflated balloon can be temporarily and resiliently deformed and compressed as described above in order for a surgeon to insert it through an aperture in a cutaneous layer of the subject.

After insertion and placement of the implantable tissue expander in a designated location in the subject, the balloon can be inflated, namely filled with liquid and/or gas until a desired volume is achieved, resulting in an implantable tissue expander with an improved tissue expansion capability. In some embodiments, when a self-sealing valve and tube are used, the tube is then preferably removed, for example, pulled out of the self-sealing valve. The balloon remains sealed by virtue of the self-sealing valve.

Following a certain time interval, typically when the surgeon appreciates that sufficient tissue expansion and tissue relaxation have been achieved, the balloon can be deflated. In some embodiments, the balloon is made from a needle-penetrable material that permits the insertion of a needle and withdrawal of the internal filling. According to these embodiments, deflation of the balloon can be performed by inserting a needle through the skin into the balloon through the balloon wall, and withdrawing the balloon filling. Upon withdrawal of the filling, the balloon remains in a deflated, collapsed form, and the rest of the implantable tissue expander, namely the foam filling enclosed within the layers described herein, serves as a filler of the expanded tissue. In some embodiments, where the balloon is inflated with gas, the natural permeability of the silicone to may allow the gas to escape from the balloon into the surrounding tissues where it is dissolved in the interstitial fluids and absorbed into the lymph and blood to be released from the body naturally. The loss of gas from the balloon gradually decreases the pressure inside the balloon and leads to its deflation, thus obviating the need described above to evacuate the liquid or gas from the balloon after the required tissue expansion has been achieved. Using this method also allows the surgeon to remove the tube during surgery.

The inclusion of a balloon in a tissue expander according to embodiments of the present invention may be particularly beneficial in primary tissue augmentation procedures, such as primary augmentation of a non-ptotic breast, with no ample skin and tissue redundancy. In such cases, in the absence of a balloon, the pressure applied on the foam-filled implant by the surrounding tissue may variably result in the deformation of the implant rather than the desired augmentation of the tissue. If an inflated balloon is present, sufficient counter-pressure is applied, thereby facilitating augmentation of the tissue overlaying the implantable tissue expander. For implantable tissue expanders intended for primary tissue augmentation, for example in primary breast augmentation, the balloon is preferably located at the posterior surface of the implant, facing the chest wall. The balloon may not be needed in procedures such as immediate reconstruction after mastectomy, replacement of an implant in a previously augmented breast, or in an augmentation-reduction procedure (mastopexy with an implant), where excess skin is available.

Thus, in some embodiments, an implantable tissue expander of the present invention includes a first compartment filled with foam and characterized by a defined, pre-determined three-dimensional configuration, and a second, flexible compartment comprising liquid filling, gas filling or a combination thereof, that is configured for controlled inflation and deflation. The first compartment according to these embodiments is configured for permanent support of an augmented tissue, and the second compartment is configured for temporary tissue expansion. It is to be understood that the term "permanent" does not indicate that the implant cannot be removed or replaced.

The size of the balloon, namely its volume at manufacturing and at inflation can vary, and is typically determined according to the type and size of the implant.

Figure 6A:
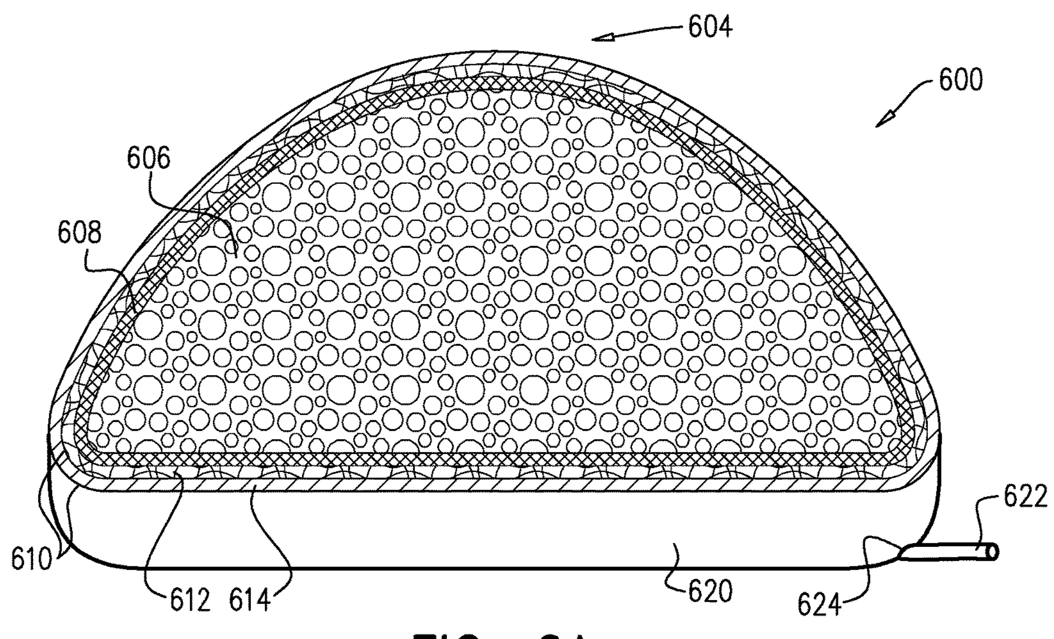
FIGS. 6A-6F. Cross-sectional illustrations of tissue expanders according to some embodiments of the present invention.
Figure 6B:
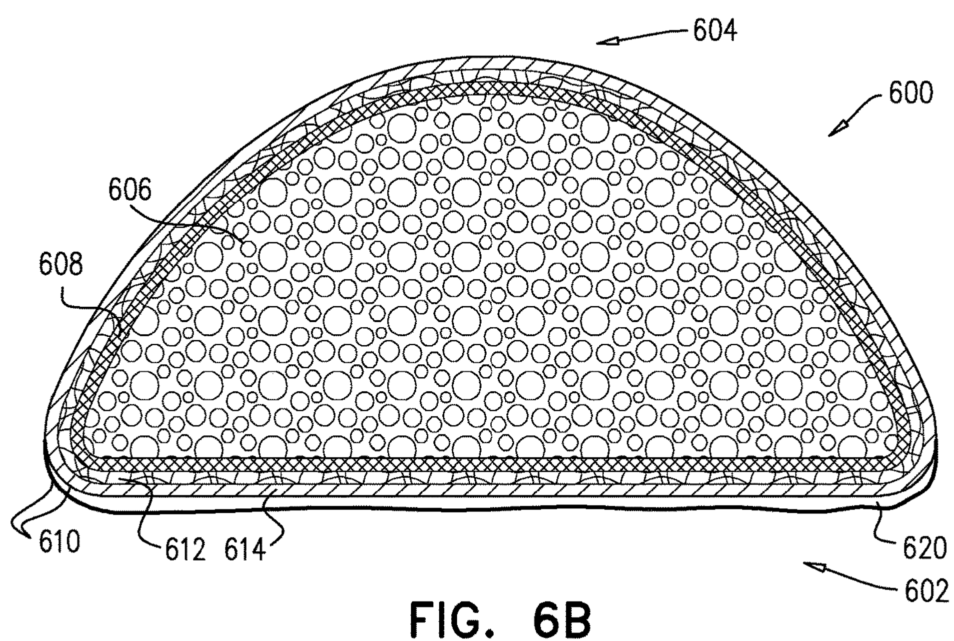

FIGS. 6A-6B illustrate cross-sectional side views of an implantable tissue expander (600) according to some embodiments of the present invention, suitable, for example, for breast augmentation and/or reconstruction, which includes an external balloon (620). The balloon is illustrated in inflated (FIG. 6A) and deflated (FIG. 6B) states.

The illustrated implantable tissue expander (600) comprises a flat base surface (602) and a convex outer surface (604) or a curved outer layer. The implantable tissue expander (600) comprises an implant inner core comprised of inner foam filling (606) enclosed within a non-stretchable resilient expansion restricting layer (608). The implantable tissue expander (600) further comprises an outer shell (610) comprising generally at least two layers (612, 614).

In FIGS. 6A-B, the illustrated tissue expander comprises an external balloon (620) affixed to the external surface of the outermost layer of the shell (614) of the implantable tissue expander, facing the flat base surface (602) of the tissue expander.

In FIG. 6A, the balloon (620) is shown in an inflated state. The balloon can be filled with a liquid, preferably a biocompatible liquid such as saline, or gas such as air. In the illustrated embodiments, a tube (622) is connected to the balloon via a self-sealing valve (624), such as a duck beak-type valve. The balloon (620) is preferably constructed from a non-porous, flexible, biocompatible material, such as silicone elastomer. The balloon (620) can be over-molded on the external surface of the shell (614) or attached to it with an adhesive or other suitable attachment means. In alternative embodiments, the balloon and the outer shell of the implant may share a common wall. For example, layer (612) enclosing the implant inner core may also constitute a wall of the balloon.

The balloon is typically shaped as an ellipsoid or elongated sphere.

The direction of expansion is generally symmetrical with the overall shape of the tissue expander, or more particularly with the shape of the foam filling, but can in principle be different, as defined by design, medical use and manufacturing processes.

In FIG. 6B, the balloon (620) is shown in an inflated state.

Figure 6C:
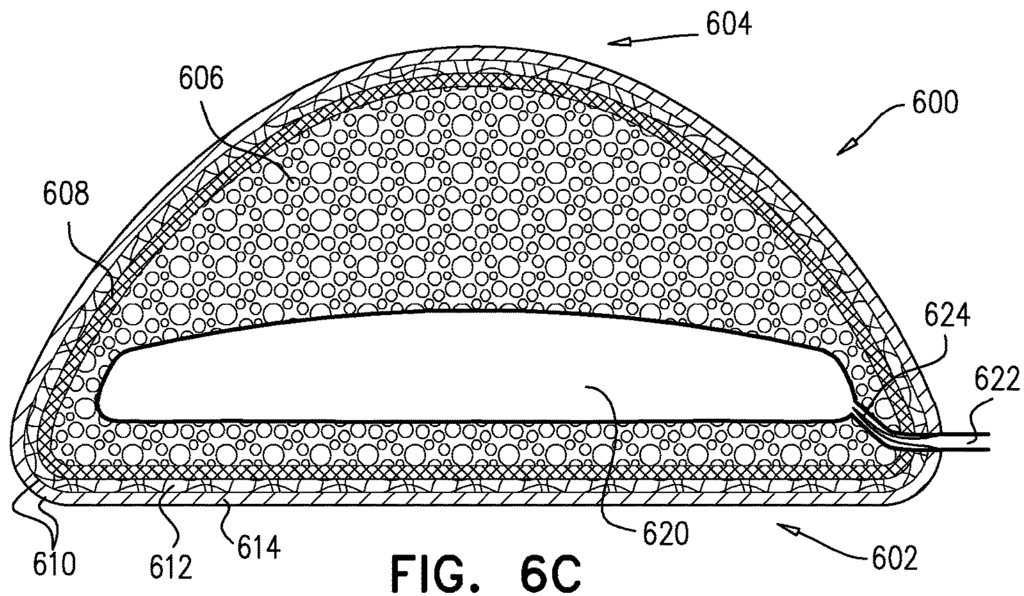

FIG. 6C illustrates a cross-sectional side view of an implantable tissue expander (600) similar to the one described in FIGS. 6A-6B, which includes an internal balloon (620) embedded within the foam filling. The balloon is illustrated in an inflated state. When inflated, the balloon applies force against the inner foam filling (606). A tube (622) is connected to the balloon via a self-sealing valve (624), such as a duck beak-type valve, and protrudes through the shell (610) of the tissue expander. In some embodiments, one end of the valve is incorporated in the wall of the balloon. Another end of the valve, configured to accommodate the tube, is in line with the outermost layer of the implant's shell. Upon filling of the balloon and removal of the tube, the valve self-seals and maintains the balloon sealed.

The illustrated balloon compartment (620) is a distinct compartment within the implant inner core, comprised of the foam filling (606) and non-stretchable resilient expansion restricting layer (608).

Figure 6D:
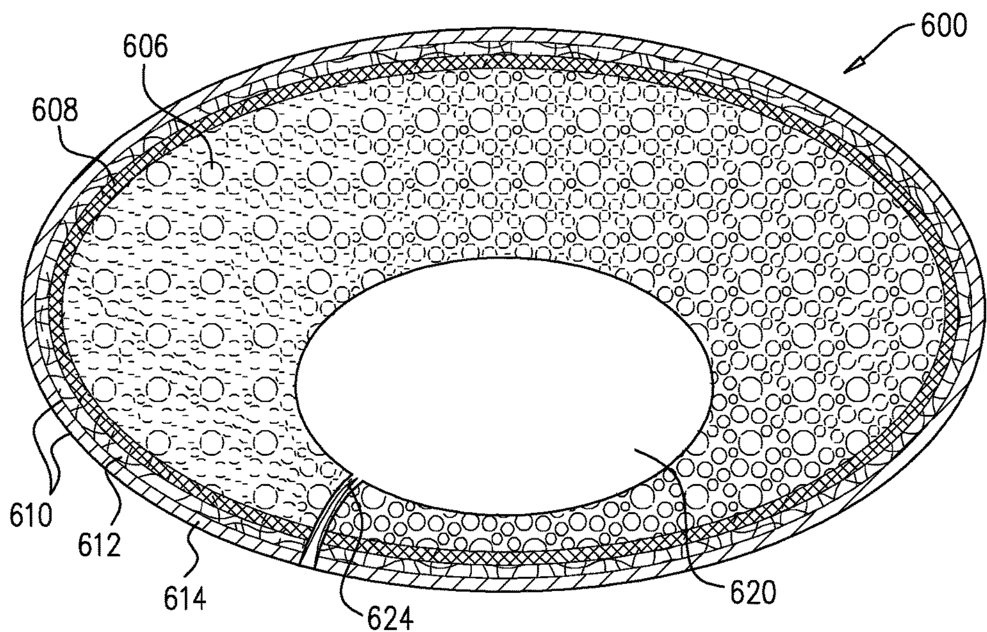

FIG. 6D illustrates another design of an implantable tissue expander (600) that contains an internal balloon as described FIG. 6C. The illustrated design is characterized by an egg-shaped configuration, and may be suitable for, instance, for lumpectomy procedures.

Figure 6E:
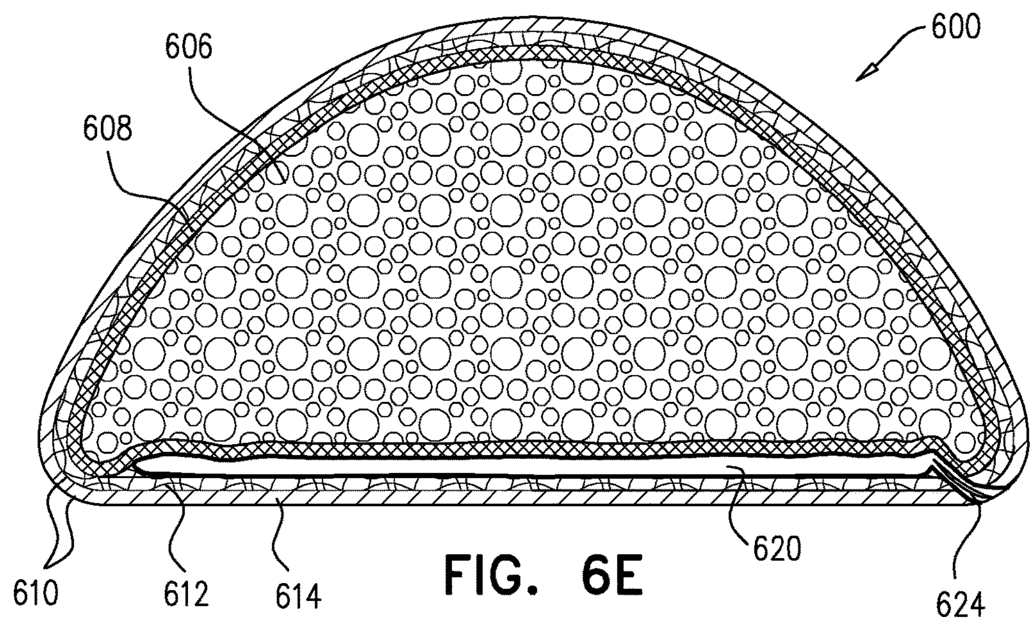
Figure 6F:
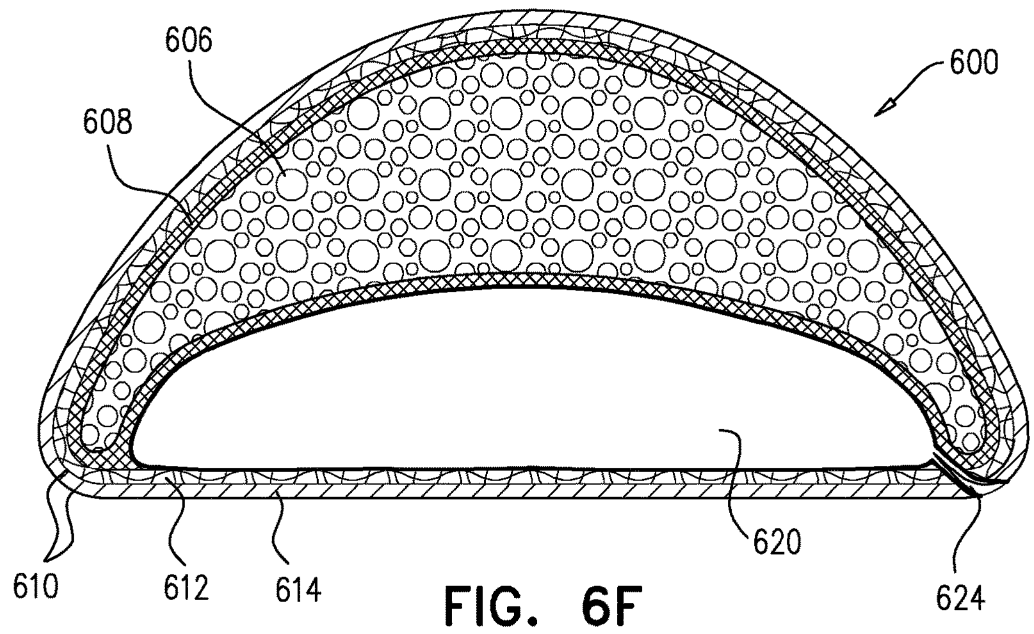

In tissue expanders according to embodiments of the present invention containing an internal balloon, the balloon may constitute an internal pocket within the implant inner core, and thus restricted by the non-stretchable resilient expansion restricting layer (608). Alternatively, as illustrated in FIGS. 6E-6F, an internal balloon may be anchored to an internal layer of the shell (612) outside the non-stretchable resilient expansion restricting layer (608), thus not restricted by it.

A tissue expander according to embodiments of the present invention may further include a plate (not shown) with an embedded, chemically etched, or laser cut for example, code/indicator identifying the tissue expander. The plate is preferably made of a biocompatible non magnetic material, such as stainless steel, or other non metallic polymers, such as polyketones (PEEK) or ceramic materials for example, which do not interfere with CT or MRI scans.

In some embodiments, a device, such as a plate, with an identifying code embedded therein is placed within the tissue expander during manufacturing. The code may be of any alphanumeric character with an optional additional symbol or design or any printable or designed sign. The plate can have a uniquely or non-uniquely identifying code. The code length can vary, thus allowing representation of a unique code if chosen once number of tissue expanders manufactured exceeds the maximal variations in a specific code length. In some embodiments, the plate can be visualized by available imaging techniques, including, inter alia, x-ray, ultrasound, C/T or MRI etc. In some embodiments, the code can be identified without the need to remove the implant from the patient's body, thus providing a registry tool and mechanism for noninvasive implant identification.

In some embodiments a passive or active electronic device, such as an RF (Radio Frequency) ID chip as a non-limiting example, can be installed in the tissue expander and used for identification of the tissue expander noninvasively by an external device communicating with the internally implanted device.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, wherein said inner foam filling is enclosed within said sealing shell, and wherein said substantially non-stretchable resilient expansion restricting layer is an outer layer surrounding said sealing shell.

2. The tissue expander of claim 1, wherein said inner foam filling is enclosed within said substantially non-stretchable resilient expansion restricting layer, and wherein said sealing shell is an outer layer surrounding said substantially non-stretchable resilient expansion restricting layer.

3. The tissue expander of claim 1, wherein said one or more layers of said sealing shell are substantially devoid of a lubricant coating.

4. The tissue expander of claim 1, further comprising a flexible sealed enclosure, enclosing said foam filling, wherein said substantially non-stretchable resilient expansion restricting layer is at least partially embedded in said flexible sealed enclosure.

5. The tissue expander of claim 1, further comprising a device with an identifying code configured for non-invasive identification of said tissue expander when implanted in a subject.

6. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, wherein said inner foam filling comprises a plurality of foam elements, wherein at least some of said plurality of foam elements are collectively enclosed within a single substantially non-stretchable resilient expansion restricting layer.

7. The tissue expander of claim 6, wherein each of said plurality of foam elements is independently enclosed within a substantially non-stretchable resilient expansion restricting layer.

8. The tissue expander of claim 6, wherein said substantially non-stretchable resilient expansion restricting layer comprises a plurality of substantially non-stretchable resilient expansion restricting layers.

9. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, and an internal skeleton element;

wherein said internal skeleton element comprises an array of elongated cells extending longitudinally between a base surface and an outer surface along mutually parallel axes and being defined by elongate cell walls formed of a resilient material.

10. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, and an internal skeleton element;

wherein said internal skeleton element comprises one or more flexible tubes.

11. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, and one or more sutures configured to retain a shape of said inner foam filling upon changes of ambient pressure, temperature or both.

12. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, and an outer mesh partially covering an outermost layer of said tissue expander, wherein said outer mesh comprises one or more mesh patches.

13. A human implantable tissue expander comprising:

an inner foam filling;

a substantially non-stretchable resilient expansion restricting layer configured to retain a fixed surface area of said foam filling upon changes of ambient pressure, temperature or both; and a sealing shell comprising one or more layers formed of a resilient material, and a balloon configured to inflate upon introduction of liquid, gas or a combination thereof into an interior thereof, and deflate upon removal of liquid, gas or a combination thereof from said interior thereof;

wherein said balloon is external to an outermost layer of the tissue expander.

14. The tissue expander of claim 13, wherein said balloon is internal to an innermost layer enclosing said foam filling.

15. The tissue expander of claim 13, wherein said balloon is between said substantially non-stretchable resilient expansion-restriction layer and the innermost layer of said sealing shell.

16. The tissue expander of claim 13, further comprising at least one of a tube and a valve communicating with said interior of said balloon.

* * * * *